United States Patent [19]
Kerry et al.

[11] 4,166,130
[45] Aug. 28, 1979

[54] PESTICIDAL COMPOSITIONS

[75] Inventors: John C. Kerry, Edwalton; David M. Weighton, Radcliffe-on-Trent, both of England

[73] Assignee: The Boots Company Limited, England

[21] Appl. No.: 911,127

[22] Filed: May 31, 1978

[30] Foreign Application Priority Data

Jun. 2, 1977 [GB] United Kingdom ............... 23351/77

[51] Int. Cl.$^2$ .......................... A01N 9/02; A01N 9/20; A01N 9/30
[52] U.S. Cl. ..................................... 424/326; 424/351
[58] Field of Search ................................ 424/326, 351

[56] References Cited

PUBLICATIONS

The Merck Index, 7th Ed., (1960), p. 1055.
Harrison et al., C.A., vol. 78, (1973), 57902k.

*Primary Examiner*—Allen J. Robinson
*Attorney, Agent, or Firm*—Gordon W. Hueschen

[57] ABSTRACT

Pesticidal compositions containing amitraz and camphechlor are described. The compositions, which comprise the active ingredients in the ratio of from 2:1 to 1:150 by weight, are synergistic and have activity against a wide range of insect and acarid pests. They are particularly useful in controlling insects on cotton crops.

12 Claims, No Drawings

PESTICIDAL COMPOSITIONS

This invention relates to a pesticidal composition and methods of controlling pests by means of it.

A problem constantly facing farmers with the need to control pests attacking crops and animals is the slow loss of activity that pesticides develop as resistance to them builds up. There is always a need for improved materials which are not only more effective against particular pests, but are also versatile and can be used to combat a wide spectrum of pests. Such improvements are seldom achieved by the use of a single pesticide.

We have now discovered that mixtures of the pesticide amitraz and camphechlor have valuable and unexpected properties. The pesticidal activity of the mixtures is greater than would be expected and synergism is exhibited of a kind which is especially effective in the context of certain crops such as cotton.

Accordingly the invention provides a pesticidal composition comprising amitraz and camphechlor in the ratio of 2:1 to 1:150 by weight.

Both amitraz, which has the chemical formula 1,5-di-(2,4-dimethylphenyl)-3-methyl-1,3,5-triazapenta-1,4-diene, and camphechlor, which is an isomeric reaction mixture of chlorinated camphenes commercially available for example as Toxaphene, are established and well-known pesticides.

The mixtures of the invention are active against a wide range of pests, both insects and acarids, and one of their advantages stems from the fact that they can be applied to a crop attacked by pests at all stages of their life cycle. This is an important advantage since the timing of pesticide application is made less critical and there is a greater chance of obtaining good, overall, control of the pests in a single treatment. In addition to their synergistic activity we have observed an extension to the spectrum of control of pests resistant to camphechlor. Amongst the pests the mixtures control are insects such as aphids for example the green peach aphid *Myzus persicae;* the boll weevil *Anthonomis grandis;* and noctuid insects such as for example the bollworm *Heliothis zea,* pink bollworm *Pectinophora gossypiella* and cotton leaf worm *Spodoptera littoralis;* and acarids (pests of the order Acarina) such as for example spider mites *Tetranychus urticae* and *Panonychus citri.* These pests attack many important crops and in doing so cause great economic damage. Thus the mixtures are especially useful on cotton, maize and soybean crops, soft fruit and top fruit such as apple, pear, peach and citrus crops.

As mentioned above, the composition of the invention finds particular application on cotton crops in which it gives excellent control of the typical pests that attack cotton. Some of the most persistent pests of this crop which frequently cause considerable damage are insects of the order Noctuidae, otherwise known as noctuids. Such pests are difficult to control and observations suggest that camphechlor which has been employed to control them is of decreasing effectiveness owing to the development of insect resistance. As a group, noctuid insects include bollworm, pink bollworm and cotton leaf worm. There are also important acarid pests such as Tetranychus spp. that attack cotton.

When employing the composition of the invention the active ingredients, amitraz and camphechlor, are mixed together in the ratio of from 2:1 to 1:150 preferably from 1:1 to 1:80 or from 1:1 to 1:40 and especially from 1:8 to 1:33 by weight. One or more additional pesticides can be added to the composition provided they do not interfere with the synergistic interaction between amitraz and camphechlor.

The composition of the invention can be employed in a wide variety of forms and can comprise a liquid or solid diluent optionally together with a surface active agent. It is most conveniently prepared in aqueous form immediately prior to use, for example, as a spray for pest-infested crops. One such method is commonly called "tank mixing" in which the two pesticide ingredients in their commercially available forms are mixed together by the farmer in a quantity of water for direct application. The concentration of the active ingredients for application to a crop by conventional ground methods is preferably within the range of from 0.001 to 10 percent, especially from 0.005 to 5 percent by weight of the composition, but more concentrated compositions containing up to 20 percent by weight may be desirable in the case of aerial sprays.

The compositions of the invention include not only those in suitable form for direct application but also concentrated primary compositions which can be supplied to the user and which require dilution with a suitable quantity of water or other diluent before application. Such compositions may comprise a surface active agent in addition to the active ingredients and typical examples are an aqueous dispersion, an aqueous emulsion, an emulsifiable concentrate, a dispersible powder or a dusting powder. As a concentrated primary composition the concentration of active ingredients can vary widely and can be for example from 5 to 95 percent by weight of the composition.

An emulsifiable concentrate, also known as a "miscible liquid ", comprises a solution of the active ingredients in a water-immiscible solvent in association with one or more emulsifying agents. An emulsion is formed with the emulsifiable concentrate is mixed with water.

A dispersible powder comprises the active ingredients in finely divided form in association with one or more dispersing agents so that a stable aqueous dispersion of the active ingredients is formed on mixing the powder with water. A finely divided inert solid diluent such as kaolin or celite is generally incorporated in the dispersible powder.

A dusting powder comprises the active ingredients intimately mixed with a solid pulverulent diluent, for example kaolin.

As a further aspect, the invention includes a method of controlling pests which comprises applying a composition comprising amitraz and camphechlor to the locus of the pests, that is, the pests or their habitat. More particularly the invention comprises a method for protecting plants from insects and acarids by the use of such compositions applied most conveniently as a foliar spray at a rate, for example. of from 0.25 to 6.0 kilograms per hectare.

A wide variety of crops including cotton, maize, soybeans, soft fruit and top fruit can be protected by treatment with the pesticidal composition of the invention, but the method of the invention finds particular application to cotton crops. Thus the invention includes a method for controlling insects on a cotton crop which comprises applying a composition of the invention to the cotton crop, in order to control, inter alia, noctuid insects such as bollworms, leaf worms and armyworms. These pests are most satisfactorily controlled by application of the active ingredients at a rate of from 0.25 to 5.0 kilograms per hectare for example from 0.5 to 2.5 kilograms per hectare. More than one application of pesticide may often be desirable and, for example, treatment at intervals of 3 to 30 days is suitable.

The invention is illustrated by the following Example.

EXAMPLE

The activity of pesticidal compositions against adults of *Tetranychus urticae* were tested according to the following procedure.

French bean leaf discs, 2 cm in diameter, were cut to retain the petiole which was kept in contact with water throughout the test. Fifteen adult mites of *Tetranychus urticae* were placed on a leaf disc, which was then sprayed to the point of run-off with an aqueous solution or dispersion of amitraz and camphechlor, both separately and together as mixtures. Percentage mortality was recorded after 72 hours.

The activity of each active component was read from dose response curves and an expected value for the mixture calculated. A comparison of these values with the data observed demonstrates that the mixtures have a synergistic effect.

| Amitraz (ppm) | Activity mortality (%) | Camphechlor (ppm) | Activity mortality (%) | Calculated effect of mixture (%) | Observed effect of mixture (%) |
|---|---|---|---|---|---|
| 240 | 52 | 2000 | 7 | 59 | 87 |
| 150 | 35 | 5000 | 14 | 49 | 95 |
| 120 | 31 | 1000 | 4 | 35 | 93 |
| 75 | 18 | 2500 | 8 | 26 | 88 |
| 60 | 17 | 8000 | 17 | 34 | 73 |
| 40 | 6 | 200 | 1 | 7 | 44 |
| 30 | 4 | 4000 | 12 | 16 | 79 |
| 25 | 2 | 500 | 2 | 4 | 35 |
| 10 | 0 | 800 | 3 | 3 | 49 |

What is claimed is:

1. An insecticidal and acaricidal composition comprising a mixture of 1,5-di-(2,4-dimethylphenyl)-3-methyl -1,3,5-triazapenta-1, 4-diene and comphechlor, in the ratio of 2:1 to 1:150 by weight, and in an insecticidally and acaricidally effective amount.

2. A composition according to claim 1, wherein the ratio is 1:1 to 1:40 by weight.

3. A composition according to claim 2, wherein the ratio is 1:8 to 1:33 by weight.

4. A method of controlling insect and acarid pests which comprises applying to the pests or their habitat an insecticidally and acaricidally effective amount of a composition comprising a mixture of 1,5-di-(2,4-dimethylphenyl)-3-methyl-1,3,5-triazapenta-1,4-diene and camphechlor, in the ratio of 2:1 to 1:150 by weight.

5. A method of controlling insect and acarid pests according to claim 4, wherein the habitat is plants and the ratio is 1:1 to 1:40 by weight.

6. A method of controlling insect and acarid pests according to claim 5, wherein the ratio is 1:8 to 1:33 by weight.

7. A method according to claim 5, wherein the plants are cotton plants.

8. A method according to claim 7, wherein the rate of application of the said mixture is 0.5 to 2.5 kilograms per hectare.

9. An insecticidal and acaricidal composition comprising a mixture of 1,5-di-(2,4-dimethylphenyl)-3-methyl-1,3,5-triazapenta-1,4-diene and comphechlor, in the ratio of 1:5 to 1:150 by weight, providing the concentration of the 1,5-di-(2,4-dimethylphenyl)-3-methyl-1,3,5-triazapenta-1,4-diene is 10 to 240 parts per million.

10. A composition according to claim 9 wherein the 1,5-di(2,4-dimethylphenyl)-3-methyl-1,3,5-triazapenta-1,4-diene is present at a concentration of 30 to 150 parts per million.

11. A method of controlling insect and acarid pests which comprises applying to the pests or their habitat a pesticidally-effective amount of a composition comprising a mixture of 1,5-di-(2,4-dimethylphenyl)-3-methyl-1,3,5-triazapenta-1,4-diene and comphechlor, in the ratio of 1:5 to 1:150 by weight, providing the concentration of the 1,5-di(2,4-dimethylphenyl)-3-methyl-1,3,5-triazapenta-1,4-diene is at least 10 parts per million.

12. The method according to claim 11 wherein the concentration of the 1,5-di(2,4-dimethylphenyl)-3-methyl-1,3,5-triazapenta-1,4-diene is 30 to 150 parts per million.

* * * * *